US00PP11351P

United States Patent [19]

Boeder

[11] Patent Number: Plant 11,351

[45] Date of Patent: Apr. 18, 2000

[54] CHRYSANTHEMUM PLANT NAMED 'SWAN'

[75] Inventor: Mark Boeder, West Wittering, United Kingdom

[73] Assignee: Cleangro Limited, West Sussex, United Kingdom

[21] Appl. No.: 09/038,788

[22] Filed: Mar. 11, 1998

[51] Int. Cl.[7] ..... A01H 5/00

[52] U.S. Cl. ..... Plt./294

[58] Field of Search ..... Plt./294

*Primary Examiner*—Howard J. Locker
*Attorney, Agent, or Firm*—Christie, Parker & Hale, LLP

[57] ABSTRACT

A new variety of garden-type Chrysanthemum plant producing white daisy-type flowers with a yellow-orange disc.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Swan'.

The female parent of the new variety is the variety known as 'Star' and the male parent is an undistributed, unnamed seedling identified as 'G23-C1'. The new variety has been asexually reproduced by vegetative cuttings in Ventura County, Calif. and the distinguishing characteristics are retained through successive generations of asexual reproduction.

SUMMARY OF THE INVENTION

'Swan' is a garden-type Chrysanthemum producing white daisy-type flowers with a yellow/orange disc.

COMPARISON WITH 'STAR'

'Swan' differs from 'Star' in ray floret color.

BRIEF DESCRIPTION OF ILLUSTRATIONS

The accompanying photographs show a typical specimen of potted plant of the new variety and of flowers of the new variety, with colors being as nearly true as possible with illustrations of the type.

DESCRIPTION OF THE PLANT

Figure 1:
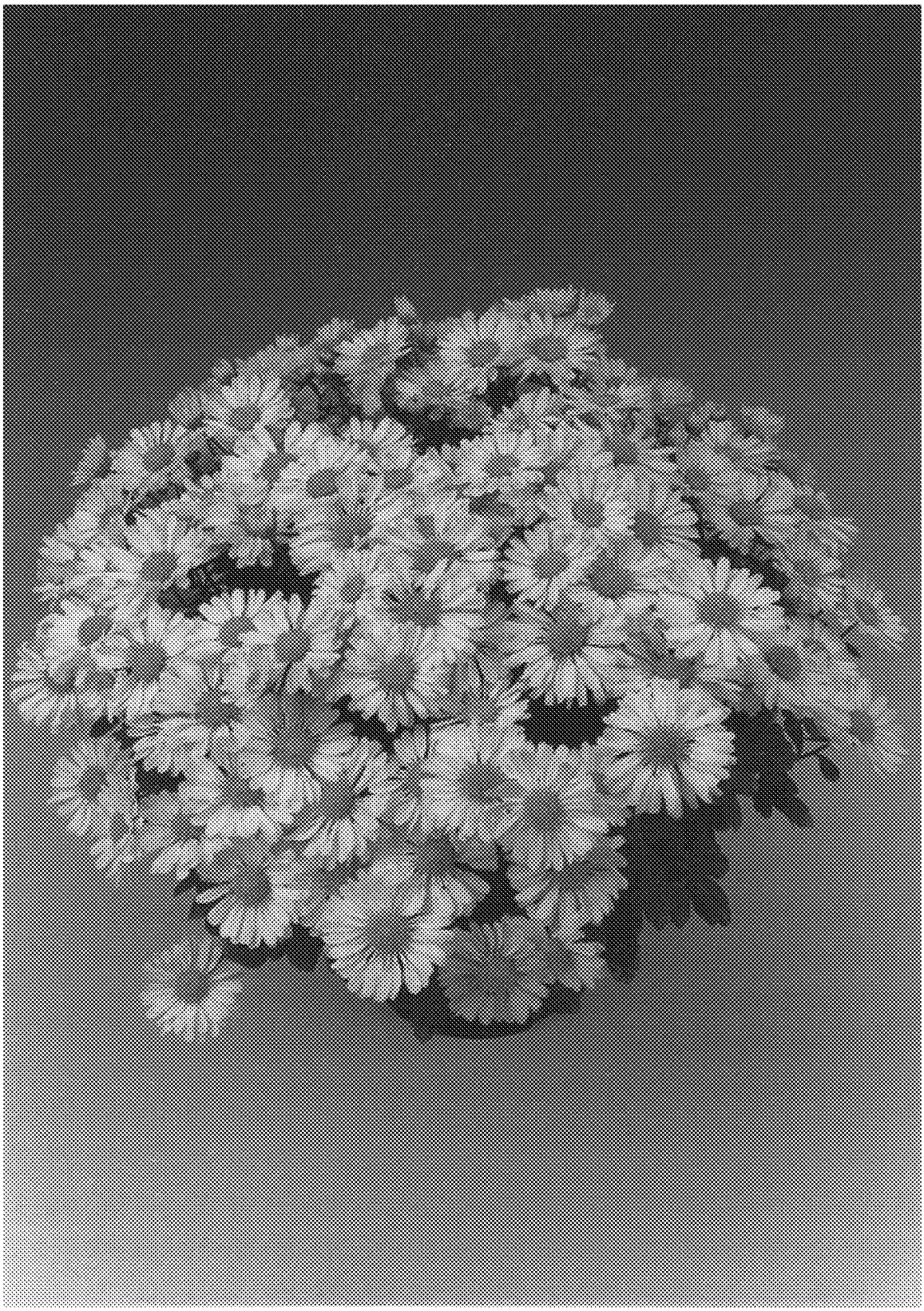
FIG. 1 is a whole plant view (from above) of the new cultivar grown in a pot.
Figure 2:
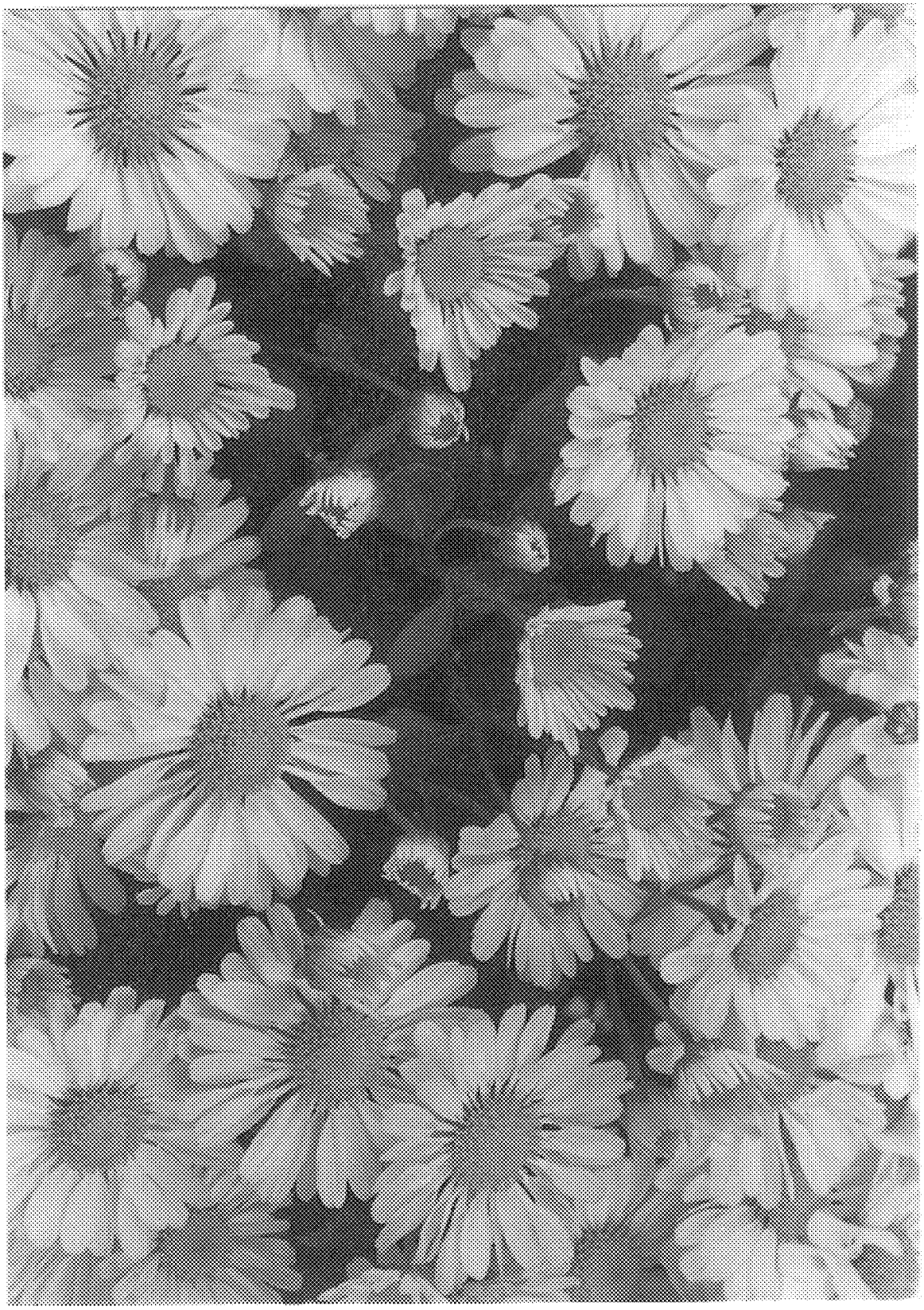
FIG. 2 shows inflorescence and foliage characteristics of the new cultivar in greater detail.

The following description of the new variety is of specimens grown in a greenhouse in Ventura County, Calif. in the month of October. 'Swan' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been ovserved that the shelf life of 'Swan' is about 29 days with the response time of about 7.5 weeks. No treatment with growth retardant is required. Useful growing conditions include night temperatures of about 64°–66° F., day temperatures of about 80°–85° F. and about 5,000 foot-candles of light.

Plant:
- *Habit.*—Mounding.
- *Height.*—About 21 cm.
- *Number of breaks from pinch.*—About 4.
- *Typical container sizes commercially grown in.*—4 inch, 6 inch 1 gallon, 3 gallon containers.
- *Length of lateral branches.*—About 18 cm.
- *Stem color.*—Near 146D.

Foliage:
- *Leaf arrangement.*—Alternate.
- *Number of leaves per lateral branch.*—About 13.
- *Leaf size.*—Length: About 6.5 cm. Width: About 3.5 cm.
- *Leaf shape.*—Ovate.
- *Attachment.*—Petioled.
- *Leaf apex.*—Obtuse.
- *Leaf base.*—Reniform.
- *Margin.*—Lobed, with small infrequent serrations.
- *Aspect.*—Flat.
- *Surface.*—Top: Pubescent. Bottom: Pubescent.
- *Petiole length.*—About 1.7 cm. Color: Near 137D.
- *Color.*—Mature leaf: Top: Near 137A. Bottom: Near 137C. Young leaf: Top: Near 137B. Bottom: Near 137C.

Flower:
- *Inflorescence form.*—Cyme.
- *Flower form.*—Daisy.
- *Number of blooms per branch.*—About 8.
- *Diameter of fully expanded bloom.*—About 5 cm.
- *Diameter of disc.*—About 1.5 cm.
- *Depth of fully expanded bloom.*—About 1.5 cm.
- *Sepal number.*—About 40. Color: Near 137C.
- *Peduncle.*—Length: Lowermost peduncles are about 8 cm and the terminal peduncle is about between 3 and 4 cm. Habit: Straight. Surface: Pubescent.
- *Flower bud shape.*—Flattened sphere. Diameter: About 0.6 cm. Height: About 0.5 cm.
- *Ray florets.*—Number per flower: About 40. Shape: Oblanceolate. Apex: Retuse. Base: Tapered, fused. Margin: Entire. Aspect: Flat. Length: About 2.2 cm. Width: About 0.5 cm.
- *Disc florets.* —Number per flower: About 165. Shape: Cylindrical. Length: About 0.5 cm. Width: About 0.1 cm.
- *Fragrance.*—Moderate.

Flower color:
- *General flower coloration.*—Pure white daisy with yellow/orange center.

*Ray florets, top side.*—Immature: Near 155A. Mature: Near 155D. Fading: Near 155D.

*Ray floret, under side.*—Immature: Near 155B. Mature: Near 155D. Fading: Near 155D.

*Disc florets.*—Immature: Near 15A. Mature: Near 13A. Fading: Near 13B.

*Changes as the flower ages.*—Disc becomes very open, releasing pollen. Ray florets become translucent, but, maintain pure white color.

Reproductive organs:

*Ray florets.*—Pistillate. Stigma shape: 2 branched. Stigma color: Near 7A. Style length: About 0.5 cm.

*Disc florets.*—Stigma shape: 2 branched. Stigma color: Near 14B. Style length: About 0.5 cm. Stamen number: About 5. Anther length: About 0.2 cm. Pollen color: Near 13B. Pollen quantity: Abundant.

What is claimed is:

1. A new and distinct Chrysanthemum plant of the variety substantially as herein shown and described.

* * * * *